(12) United States Patent
Okusa et al.

(10) Patent No.: US 9,846,170 B2
(45) Date of Patent: Dec. 19, 2017

(54) AUTOMATED ANALYZER

(71) Applicant: HITACHI HIGH-TECHNOLOGIES CORPORATION, Tokyo (JP)

(72) Inventors: Takenori Okusa, Tokyo (JP); Kazuhiro Nakamura, Tokyo (JP); Yoshihiro Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 20 days.

(21) Appl. No.: 14/373,368

(22) PCT Filed: Dec. 20, 2012

(86) PCT No.: PCT/JP2012/083132
§ 371 (c)(1),
(2) Date: Jul. 21, 2014

(87) PCT Pub. No.: WO2013/111484
PCT Pub. Date: Aug. 1, 2013

(65) Prior Publication Data
US 2015/0010436 A1    Jan. 8, 2015

(30) Foreign Application Priority Data

Jan. 23, 2012    (JP) ................................ 2012-011541

(51) Int. Cl.
*G01N 35/10* (2006.01)
*G01N 35/00* (2006.01)
*G01N 35/04* (2006.01)

(52) U.S. Cl.
CPC ... *G01N 35/00029* (2013.01); *G01N 35/0092* (2013.01); *G01N 35/04* (2013.01);
(Continued)

(58) Field of Classification Search
CPC ... G01N 35/00663; G01N 2035/00673; G01N 2035/0462
See application file for complete search history.

(56) References Cited

U.S. PATENT DOCUMENTS

| 2005/0014285 A1 | 1/2005 | Miller |
| 2005/0207938 A1 | 9/2005 | Hanawa et al. |
| 2008/0199358 A1* | 8/2008 | Yamano ................. G01N 35/04 422/68.1 |

FOREIGN PATENT DOCUMENTS

| EP | 2023150 A2 | 2/2009 |
| JP | 2004-271265 A | 9/2004 |

(Continued)

OTHER PUBLICATIONS

International Preliminary Report on Patentability received in International Application No. PCT/JP2012/083132 dated Aug. 7, 2014.
(Continued)

*Primary Examiner* — P. Kathryn Wright
(74) *Attorney, Agent, or Firm* — Mattingly & Malur, PC

(57) ABSTRACT

To provide an automated analyzer adapted for accommodating a larger number of reagent cassettes to meet calls for increases in analytical throughput and in the number of analytical items, and thus using the accommodated reagent cassettes more efficiently. An automated analyzer body 100 includes a main reagent buffer 4 for storing a plurality of reagent cassettes each containing a reagent used for analysis and a subsidiary reagent buffer 12. A reagent cassette transfer 11 transfers the reagent cassettes from the main reagent buffer to the subsidiary reagent buffer, and vice versa. A control unit 200 operates so that when a reagent cassette that is not set in the main reagent buffer is to be used for an assigned analysis, the reagent cassette for the assigned analysis is transferred from the subsidiary reagent buffer to the main reagent buffer.

6 Claims, 5 Drawing Sheets

(52) U.S. Cl.
CPC ............... *G01N 35/00663* (2013.01); *G01N 2035/00673* (2013.01); *G01N 2035/0443* (2013.01); *G01N 2035/0455* (2013.01); *G01N 2035/0462* (2013.01)

(56) References Cited

FOREIGN PATENT DOCUMENTS

| | | | |
|---|---|---|---|
| JP | 2005-037171 A | | 2/2005 |
| JP | 2007-524080 A | | 8/2007 |
| JP | 2009-036513 A | | 2/2009 |
| JP | 2009-068992 A | | 4/2009 |
| JP | 2009-068993 A | | 4/2009 |
| JP | 2009068992 A | * | 4/2009 |
| JP | 2011-013127 A | | 1/2011 |
| JP | 2012-008053 A | | 1/2012 |

OTHER PUBLICATIONS

Extended European Search Report received in corresponding European Application No. 12866882.9 dated Aug. 26, 2015.

* cited by examiner

AUTOMATED ANALYZER

TECHNICAL FIELD

The present invention relates generally to automated analyzers that automatically conduct qualitative and quantitative analyses upon blood, urine, and other biological samples. More particularly, the invention is directed to an automated analyzer suitable for a configuration with a plurality of reagent buffers provided to store reagent cassettes each containing a reagent to be used for analysis.

BACKGROUND ART

In recent years, daily analytical throughput in one analyzer tends to increase, and also does the number of analyzable test items required for one analyzer. With the increases in analytical throughput and in the number of test items, there are increasing tendencies in the quantities and kinds of reagents to be set in the analyzer. As a result, it is requested that a larger number of reagent cassettes be set in the device and that the set reagent cassettes be used more efficiently.

Methods for setting a larger number of reagent cassettes in a device and using these reagent cassettes more efficiently include known techniques that employ a plurality of reagent buffers.

For example, firstly, an automated analyzer with a main reagent buffer and a subsidiary reagent buffer is known (refer to Patent Document 1, for example). In this known automated analyzer, a reagent cassette in which a residual amount of usable reagent has become too small for analysis is removed from the main reagent buffer, then another reagent cassette transferred from the subsidiary reagent buffer is set in the vacancy.

Secondly, an automated analyzer with a plurality of reagent buffers and a reagent pipetter disposed for each of the reagent buffers is known (refer to Patent Document 2, for example).

PRIOR ART DOCUMENTS

Patent Documents

Patent Document 1: JP-2005-37171-A
Patent Document 2: JP-2007-524080-A

SUMMARY OF THE INVENTION

Problems to be Solved by the Invention

In the device according to Patent Document 1, however, not until the reagent cassette with only a small residual amount of reagent has been removed from the main reagent buffer will the reagent cassette within the subsidiary reagent buffer be transferred to the main reagent buffer and have the reagent used for the analysis. This means that the reagent set in the subsidiary reagent buffer cannot be used at a desired time for the analysis.

In addition, in the device according to Patent Document 2, a need arises to reserve a reagent pipetter mounting region for each reagent buffer, so that regions usable for setting the reagent cassettes will correspondingly narrow.

An object of the present invention is to provide an automated analyzer adapted for accommodating a larger number of reagent cassettes to meet calls for increases in analytical throughput and in the number of analytical items, and thus using the accommodated reagent cassettes more efficiently.

Means for Solving the Problems (1) An automated analyzer that the present invention provides as an aspect thereof to attain the above object includes: a main reagent buffer for storing a plurality of reagent cassettes each containing a reagent used for analysis; a reagent pipetter for pipetting a desired reagent from the main reagent buffer; a subsidiary reagent buffer for storing a plurality of reagent cassettes each containing a reagent used for analysis; a reagent cassette transfer for transferring the reagent cassettes from the main reagent buffer to the subsidiary reagent buffer, and vice versa; a plate disposed on the main reagent buffer for moving the reagent cassettes; and a control unit configured to control operation of the reagent cassette transfer, wherein the control unit operates so that when a reagent cassette that is not set in the main reagent buffer is to be used for an assigned analysis, the reagent cassette for the assigned analysis is transferred from the subsidiary reagent buffer to the main reagent buffer.

With the above configuration, a larger number of reagent cassettes can be set to meet calls for increases in analytical throughput and in the number of analytical items, and thus the set reagent cassettes can be used more efficiently.

(2) In item (1) described above, the control unit preferably schedules ordering of analyses so that the analyses using the reagent cassettes placed on the same plate for a plurality of biological samples will be continuously executed, the biological samples being continuously analyzed with a plurality of analytical request items assigned therefor.

(3) In item (1), the control unit preferably transfers a calibrated reagent cassette from the main reagent buffer to the subsidiary reagent buffer.

(4) In item (1), the control unit preferably transfers an uncalibrated reagent cassette that is set in the subsidiary reagent buffer, from the subsidiary reagent buffer to the main reagent buffer, before a time at which the reagent cassette is estimated to be used.

(5) In item (1), when the amount of usable reagent left in the reagent cassette set in the main reagent buffer decreases below a predetermined level, the control unit preferably transfers the reagent cassette for the analysis stored in the subsidiary reagent buffer to the main reagent buffer.

(6) In item (1), the control unit preferably unloads reagent cassettes set in the main reagent buffer or the subsidiary reagent buffer from the device, the reagent cassettes containing no residual amount of usable reagent needed for analysis or having exceeded expiration date.

(7) In item (1), the control unit preferably unloads from the device the reagent cassettes set in the main reagent buffer or the subsidiary reagent buffer in accordance with an instruction from an operator.

(8) In item (1), the control unit preferably transfers a reagent cassette from the main reagent buffer to the subsidiary reagent buffer, or vice versa, in accordance with an instruction from the operator.

(9) An automated analyzer that the present invention provides as the aspect thereof to attain the above object includes: a main reagent buffer for storing a plurality of reagent cassettes each containing a reagent used for analysis; a reagent pipetter for pipetting a desired reagent from the main reagent buffer; a subsidiary reagent buffer for storing a plurality of reagent cassettes each containing a reagent used for analysis; a reagent cassette transfer for transferring the reagent cassettes from the main reagent buffer to the subsidiary reagent buffer, and vice versa; a plate disposed on the main reagent buffer for moving the reagent cassettes; and a control unit configured to control operation of the reagent cassette transfer, wherein a priority assignments table is provided in the control unit, the priority assignments table defining priority levels used for the analyses, and the control unit stores reagent cassettes of higher priority levels into the main reagent buffer according to priority levels defined in the priority assignments table.

With the above configuration, a larger number of reagent cassettes can be set to meet calls for increases in analytical throughput and in the number of analytical items, and thus the set reagent cassettes can be used more efficiently.

(10) In item (9) described above, the control unit preferably is further configured to store information about analytical items that have been executed within a definite period of time, and preferentially store reagent cassettes into the main reagent buffer, the reagent cassettes executed more often than others within the definite period of time.

(11) In item (9), the control unit preferably calibrates uncalibrated reagent cassettes of all reagent cassettes set in the main reagent buffer or the subsidiary reagent buffer.

(12) In item (9), the control unit preferably determines whether QC (quality control) is to be conducted upon the reagent cassettes set in the main reagent buffer or the subsidiary reagent buffer, and executes the QC if necessary.

(13) In item (9), the control unit preferably presents, to an operator, reagent information on the reagent cassettes set in the main reagent buffer and the subsidiary reagent buffer.

(14) An automated analyzer that the present invention provides as the aspect thereof to attain the above object includes: a main reagent buffer for storing a plurality of reagent cassettes each containing a reagent used for analysis; a reagent pipetter for pipetting a desired reagent from the main reagent buffer; a subsidiary reagent buffer for storing a plurality of reagent cassettes each containing a reagent used for analysis; a reagent cassette transfer for transferring the reagent cassettes from the main reagent buffer to the subsidiary reagent buffer, and vice versa; plates disposed on the main reagent buffer for moving the reagent cassettes; and a control unit configured to control operation of the reagent cassette transfer, wherein when the number of reagent cassette-setting positions without a reagent cassette on the plates of the main reagent buffer becomes less than values predefined for each of the plates, the control unit unloads reagent cassettes from the main reagent buffer and transfers the unloaded reagent cassettes to the subsidiary reagent buffer, until the number of reagent cassette-setting positions without a reagent cassette on the plates has become equal to or larger than the values predefined for each of the plates.

With the above configuration, a larger number of reagent cassettes can be set to meet calls for increases in analytical throughput and in the number of analytical items, and thus the set reagent cassettes can be used more efficiently.

(15) In item (14) described above, the control unit preferably transfers, from the main reagent buffer to the subsidiary reagent buffer, reagent cassettes for which no analysis is assigned during a definite time from a start of the transfer.

(16) In item (14), the control unit is preferably configured to preferentially transfer, from the main reagent buffer to the subsidiary reagent buffer, reagent cassettes having longer time being unused for an analysis from a starting time of the transfer.

Effects of the Invention

In accordance with the present invention, a larger number of reagent cassettes are set to meet calls for increases in analytical throughput and in the number of analytical items, and thus the set reagent cassettes are used more efficiently.

MODES FOR CARRYING OUT THE INVENTION

Hereunder, a configurational description and operational description of an automated analyzer according to an embodiment of the present invention will be given using FIGS. 1 to 5.

First, an overall configuration of the automated analyzer according to the present embodiment is described below using FIG. 1.

Figure 1:
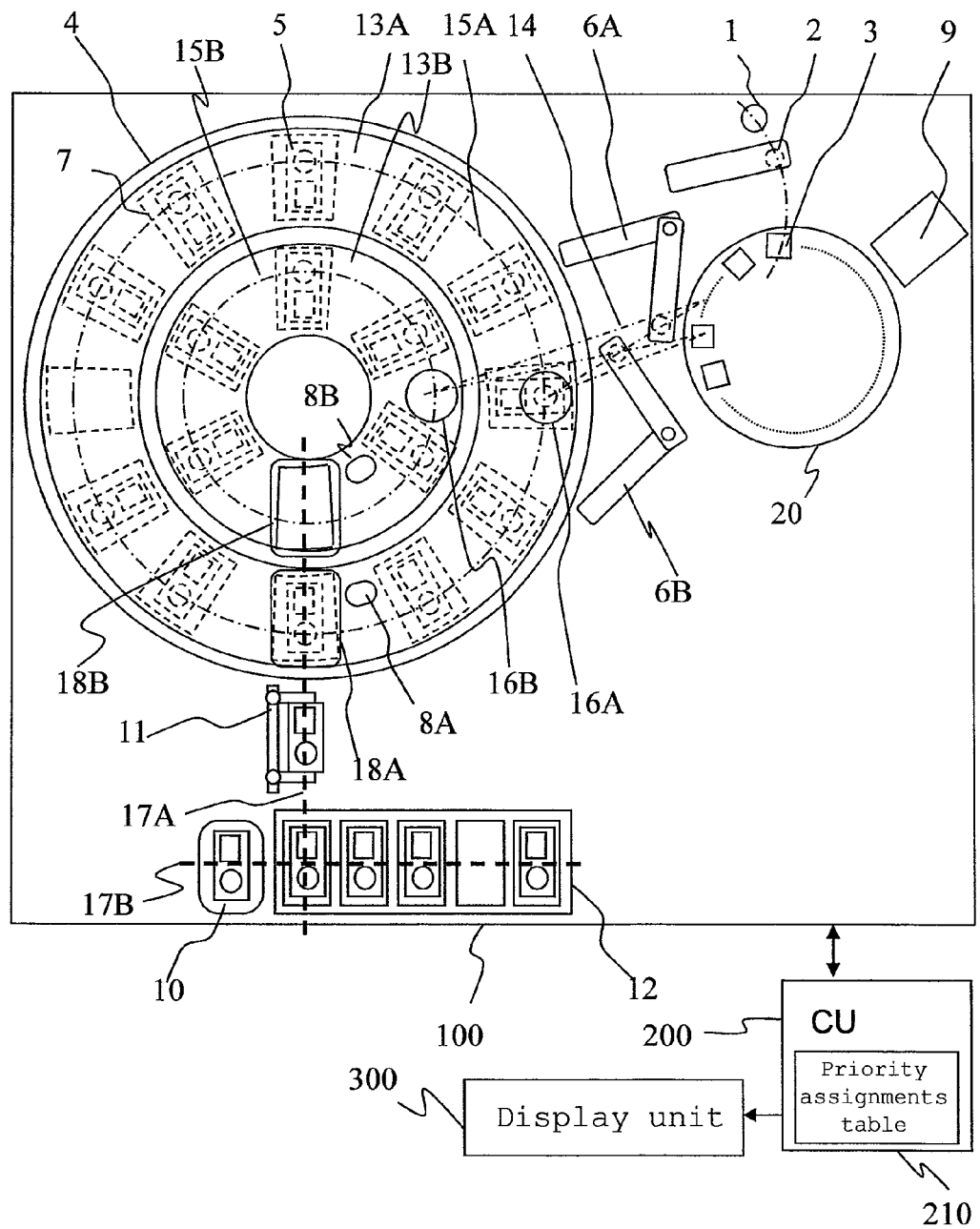
FIG. 1 is a plan configuration diagram showing an overall configuration of an automated analyzer according to an embodiment of the present invention.

FIG. 1 is a plan configuration diagram showing the overall configuration of the automated analyzer according to the present embodiment.

The automated analyzer of the present embodiment includes an automated analyzer body 100 and a control unit 200. The automated analyzer of the present embodiment has a function that conducts qualitative and quantitative analyses upon specific chemical components contained in a biological sample, or upon biologically derived substances contained in the sample.

A sample container with the hermetically enclosed biological sample such as blood is set in a sample container hold position 1 automatically by a sample transport device. An operator may set this sample container in the sample container hold position 1 by hand.

A plurality of reaction vessels 3 are placed in a circumferential direction on a reaction disk 20. The reaction disk 20 can be rotated to move the placed reaction vessels 3 to sampling positions and reagent-pipetting positions or to photometry positions of reaction liquids obtained. An incubation bath is placed under the reaction disk 20, and the reaction vessels 3 are each immersed in the incubation bath.

The biological sample within the sample container set in the sample container hold position 1 is pipetted into one of the reaction vessels 3 by a sample pipetter 2.

The automated analyzer body 100 of the present embodiment includes two reagent buffers, namely a main reagent buffer 4 and a subsidiary reagent buffer 12, to store reagent cassettes each containing a reagent to be used for analysis. The buffers 4, 12 are both temperature-controlled since reagents need to be stored under an environment of a certain temperature range so as to maintain performance characteristics of the reagents.

The main reagent buffer 4 includes a first plate 13A and a second plate 13B, both arranged in concentric form and having a shape of a ring. A plurality of reagent cassettes 5 are set on each of the plates 13A, 13B. The plates 13A, 13B can both be rotated independently of each other. Two reagent pipetters, 6A and 6B, are placed at positions between, and near, the main reagent buffer 4 and the reaction disk 20. The reagent pipetters 6A, 6B can aspirate the reagents from the reagent cassettes set on the plates 13A, 13B, and pipette the reagents into the reaction vessels 3 held on the reaction disk 20. The reagent pipetters 6A, 6B each include a first arm and a second arm, both articulated and pivotally held, so the pipetters have flexibility of their moving zones, compared with those of a non-articulated type. Accordingly, the reagent pipetter 6A can pipette the reagents set on the plates 13A, 13B, into part of the reaction vessels 3. The reagent pipetter 6B can likewise pipette the reagents set on the plates 13A, 13B, into a reminder of the reaction vessels 3.

In the above manner, the reagents in the reagent cassettes of the main reagent buffer are pipetted into the reaction vessels 3 according to analytical item by the reagent pipetters 6A, 6B.

Prior to a start of reagent pipetting, one of the reagent cassettes 5 is set in a reagent cassette-setting position of the main reagent buffer 4. A reagent cassette scanner 8A, 8B reads corresponding reagent information from a tag or bar code affixed to the cassette 5.

The reaction liquid, a mixture of the biological sample and reagent in one reaction vessel 3, has its temperature and other environmental parameters controlled, and is further provided with necessary operations such as mixing, for accelerated chemical reaction. The chemical reaction is repeated once or a plurality of times, depending on the analytical item. After the necessary chemical reaction(s), spectral photometry, absorption photometry, or fluorescent photometry takes place and the components contained in the sample are analyzed from measurement results.

A reagent cassette transfer 11 is placed between the main reagent buffer 4 and the subsidiary reagent buffer 12. The reagent cassette transfer 11 can transfer a reagent cassette along reagent cassette movement paths 17A, 17B. A reagent cassette insertion port 10 is disposed adjacently to the subsidiary reagent buffer 12.

After a reagent cassette 5 has been inserted from the reagent cassette insertion port 10 into the device by the operator, the reagent cassette transfer 11 transfers the reagent cassette 5 to the main reagent buffer 4 or the subsidiary reagent buffer 12, for storage.

The main reagent buffer 4 has a cover on its upper surface. The cover minimizes any effects of outside air upon the air-conditioned (cooled) reagent cassettes within the main reagent buffer 4. The cover has reagent suction ports 16A and 16B that accept nozzle ends of the reagent pipetters 6A, 6B, and reagent cassette loading/unloading ports 18A and 18B that enable the transfer of the reagent cassettes 5.

The reagent suction port 16A is provided at a crossing point between a movement path 14 of the nozzle of the reagent pipetter 6A or 6B and a movement path 15A of a suction port for one of the reagent cassettes 5 on the plate 13A. This crossing point is present on the main reagent buffer 4. The reagent suction port 16B is likewise provided at a crossing point between a movement path 14 of the nozzle of the reagent pipetter 6A or 6B and a movement path 15B of a suction port for another one of the reagent cassettes 5 on the plate 13B. This crossing point is also present on the main reagent buffer 4. When a reagent is pipetted, the plate 13A or 13B moves and thus a reagent cassette 5 containing the reagent needed for desired analysis is moved to the reagent suction port 16A or 16B. After the movement of the reagent cassette 5, the nozzle of the reagent pipetter 6A or 6B aspirates the reagent from the reagent suction port 16A or 16B. At least one reagent suction port, 16A or 16B, is provided on each plate.

The transfer of reagent cassettes between the main reagent buffer 4 and the subsidiary reagent buffer 12 is conducted by the reagent cassette transfer 11. The reagent cassette loading/unloading port 18A is formed at a crossing point between the movement path 15A of a reagent cassette-setting position 7 and the reagent cassette movement path 17A of the reagent cassette transfer 11. This crossing point is present on the main reagent buffer 4. The reagent cassette loading/unloading port 18B is likewise formed at a crossing point between the movement path 15B of the reagent cassette-setting position 7 and the reagent cassette movement path 17A of the reagent cassette transfer 11. This crossing point is also present on the main reagent buffer 4. The reagent cassette loading/unloading ports 18A, 18B are provided on the plates 13A, 13B, respectively. The reagent cassette 5 is loaded into/unloaded from the main reagent buffer 4 through the reagent cassette loading/unloading port 18A or 18B by the reagent cassette transfer 11.

The transfer of a reagent cassette from the subsidiary reagent buffer 12 to the main reagent buffer 4 is conducted in the following sequence.

First, the reagent cassette transfer 11 transfers a desired reagent cassette from the subsidiary reagent buffer 12 to the reagent cassette loading/unloading port 18 (18A or 18B) of the main reagent buffer 4. Simultaneously with or before or after the transfer, a reagent cassette-setting position 7 without a reagent cassette in the main reagent buffer 4 is moved to the reagent cassette loading/unloading port 18. After this, the reagent cassette is set in the reagent cassette-setting position by the reagent cassette transfer 11.

After the setting of the reagent cassette in the main reagent buffer 4 or before or after the transfer of the reagent cassette by the reagent cassette transfer 11, the reagent cassette scanner 8A, 8B, such as an RFID reader or a barcode reader (BCR), conducts a reagent information read/write process upon the reagent cassette by scanning the cassette-affixed tag or bar code. It is thus confirmed that the reagent cassette is the desired reagent cassette.

The reagent information here includes a name of the reagent, the amount of usable reagent left, analytical parameters, an expiration date of the reagent, a history of movements between the main reagent buffer and the subsidiary reagent buffer. In addition, the reagent cassette scanner 8A, 8B, such as an RFID reader or a barcode reader (BCR), may be disposed in the main reagent buffer 4, as shown in FIG. 1, or may exist in at least one of, for example, the main reagent buffer, the subsidiary reagent buffer, and the reagent cassette transfer.

Next, a sequence for transferring a reagent cassette from the main reagent buffer 4 to the subsidiary reagent buffer 12 is described below.

First, a desired reagent cassette is moved to the reagent cassette loading/unloading port 18 (18A or 18B), in the main reagent buffer 4. Simultaneously with or before or after the transfer, the reagent cassette transfer 11 moves to the reagent cassette loading/unloading port 18. After this movement, the reagent cassette transfer 11 unloads the reagent cassette from the reagent cassette loading/unloading port 18 of the main reagent buffer 4 and transfers the reagent cassette to the subsidiary reagent buffer 12.

Before the unloading of the reagent cassette from the main reagent buffer 4 or before or after the transfer of the reagent cassette by the reagent cassette transfer 11, the reagent cassette scanner 8A, 8B, such as an RFID reader or a barcode reader (BCR), conducts a reagent information read/write process upon the reagent cassette by scanning the cassette-affixed tag or bar code. It is thus confirmed that the reagent cassette is the desired reagent cassette.

The control unit 200 of the analyzer recognizes all the reagent information relating to reagent cassettes set in the main reagent buffer 4 and the subsidiary reagent buffer 12. The control unit 200 also presents the reagent information to the operator by displaying it on a display unit 300 shown in FIG. 1. The displayed reagent information is used for the operator to perform operations such as specifying analytical items and instructing the unloading of specific reagent cassettes set in both buffers. The operator can remove, for example, a reagent cassette not containing a sufficient amount of reagent for conducting a new analysis, or a reagent cassette that still contains a sufficient amount of reagent for analysis, but is to be temporarily removed. The removal of these reagent cassettes can be performed by giving instructions based on the displayed reagent information. In addition, a specific reagent cassette in the main reagent buffer can be moved to the subsidiary reagent buffer, or conversely a reagent cassette in the subsidiary reagent buffer can be moved to the main reagent buffer.

Details of control relating to reagent cassette loading into and unloading from the main reagent buffer in the automated analyzer according to the present embodiment are described below using FIG. 2.

Figure 2:
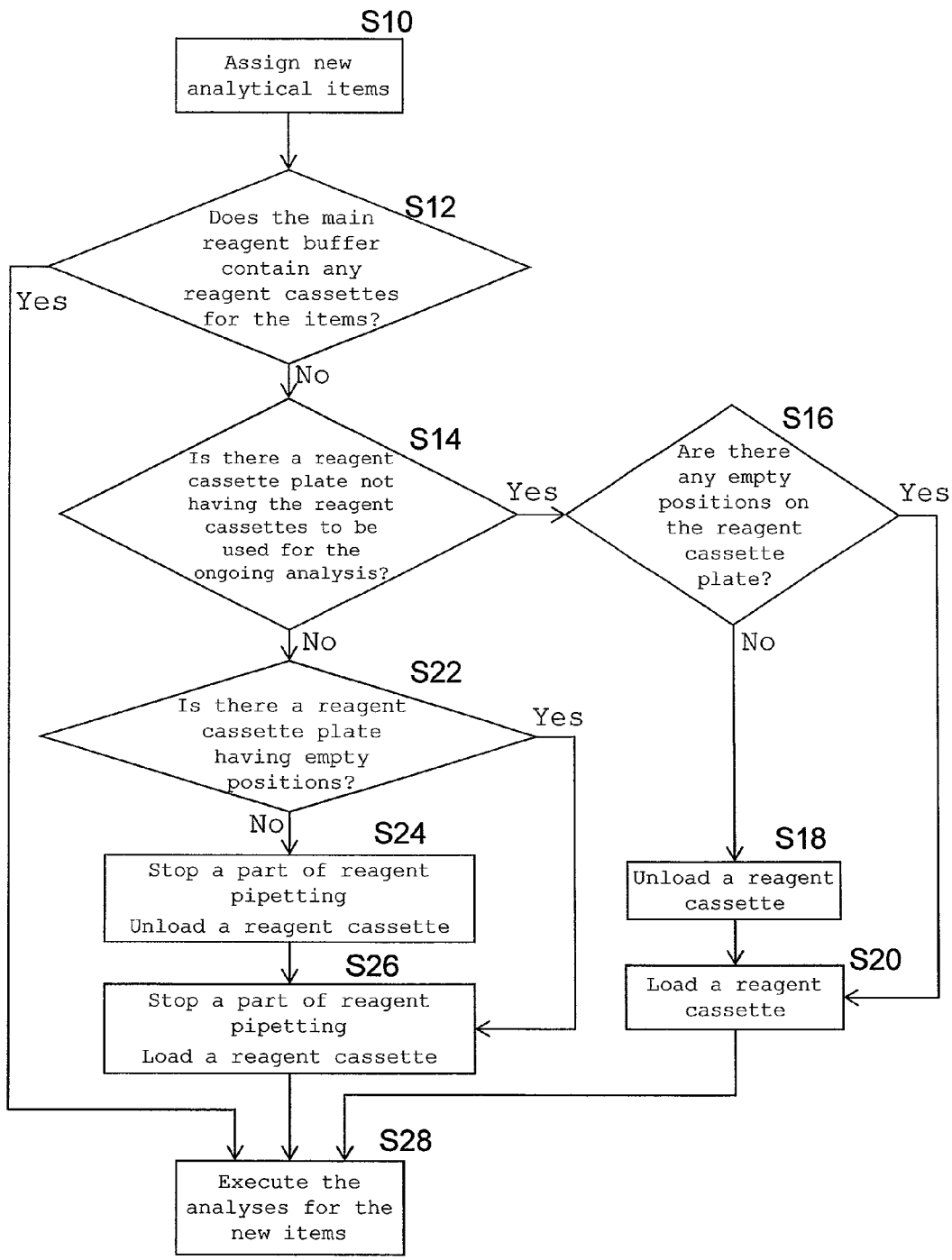
FIG. 2 is a flowchart that shows details of control relating to reagent cassette loading into and unloading from a main reagent buffer in the automated analyzer according to the embodiment.

FIG. 2 is a flowchart showing the details of the control relating to reagent cassette loading into and unloading from the main reagent buffer in the automated analyzer according to the embodiment.

New analytical items are assigned in step S10. More specifically, analytical items to be executed for given biological samples are requested for each of the biological samples by the operator or from a host to which the automated analyzer is connected. In this step, the analysis using the reagents placed in the subsidiary reagent buffer 12 is requested in addition to the analysis using the reagents placed in the main reagent buffer 4. Detailed information on these newly assigned analytical items is stored into the control unit 200.

The control unit 200 then determines in step S12 whether the reagent cassettes holding the reagents to be used for the requested analytical items are placed in the main reagent buffer 4. If the reagent cassettes are placed, processing skips to step S28, in which the analyses for the new analytical items are then conducted. If the reagent cassettes are not placed, processing advances to step S14.

If the reagent cassettes holding the reagents to be used for the requested analytical items are not placed in the main reagent buffer 4, the control unit 200 determines in step S14 whether there is a reagent cassette plate not having thereon the reagent to be used for the analysis that follows the ongoing analysis. Assume, for example, that analytical item A is currently being executed and that while reagent "a" for this item is placed on the first plate 13A, reagent "a" is not placed on the second plate 13B. In this example, the second plate 13B is equivalent to the reagent cassette plate not having thereon the reagent to be used for the analysis that follows the ongoing analysis. If the plate is present, processing advances to step S16. If the plate is absent, processing skips to step S22.

If a plate not being used for the ongoing analysis is present in the main reagent buffer 4, the control unit 200 determines in step S16 whether an empty position exists on that reagent cassette plate (in the above example, the second plate 13B). The empty position refers to a location on the plate 13B where a reagent cassette is not placed. If the empty position is present, processing skips to step S20. If the empty position is absent, processing advances to step S18.

If the empty position exists in the main reagent buffer 4, the control unit 200 uses the reagent cassette transfer 11 in step S18 to unload a reagent cassette from the subsidiary reagent buffer 12.

The reagent cassette unloaded here will be selected from the following candidates. In an example, if there is a reagent cassette containing an expired reagent, this cassette will be unloaded. Further, in another example, if the amount of usable reagent left in a reagent cassette is too small for the next analysis, that is, reagent amount level is low, this cassette will be unloaded. In yet another example, if there is a reagent for which the analysis is not assigned for more than a definite time (i.e., more than a time required for the reagent cassette to be reloaded after being unloaded), that is, if there is a reagent whose pipetting is not needed for the definite time requirement from unloading to reloading, that reagent cassette will be unloaded. In a further example, a reagent cassette containing a reagent infrequently used will be unloaded.

Upon completion of step S18 or if in step S16 the empty position is determined to be present, the control unit 200 uses the reagent cassette transfer 11 in step S20 to load the unloaded reagent cassette into the main reagent buffer and set the loaded reagent cassette in the empty position. After this, in step S28, the control unit 200 executes the analyses for the new analytical items.

Conversely, if in step S14 a plate being used for the ongoing analysis is present in the main reagent buffer 4, that is, a plate being used for the ongoing analysis is present, then the control unit 200 determines in step S22 whether an empty position exists on that reagent cassette plate (in the foregoing example, the first plate 13A).

If an empty position exists in the main reagent buffer 4, in step S24 the control unit 200 brings reagent pipetting to a temporarily stop and after this, uses the reagent cassette transfer 11 to unload a reagent cassette from the subsidiary reagent buffer 12.

In next step S26, the control unit 200 uses the reagent cassette transfer 11 to load the unloaded reagent cassette into the main reagent buffer and set the loaded reagent cassette in the empty position. After this, in step S28, the control unit 200 executes the analyses for the new analytical items.

As described above, if the analysis using a reagent cassette not set in the main reagent buffer 4 is requested, this reagent cassette is transferred from the subsidiary reagent buffer 12 to the main reagent buffer 4 by the reagent cassette transfer 11 and then the corresponding analysis is conducted. Execution of this sequence allows not only a reagent cassette in the main reagent buffer, but also a reagent cassette in the subsidiary reagent cassette, to be used for the desired analyses.

In addition, while an analysis is being conducted, if the number of untested items relating to a reagent cassette in the main reagent buffer 4 decreases below a specified minimum allowable value, that reagent cassette is transferred from the subsidiary reagent buffer 12 to the main reagent buffer 4. If the reagent is not set in the subsidiary reagent buffer 12, information indicating that the number of untested items has decreased below the specified minimum allowable value is presented in the form of characters, a sound, or the like, to the operator or the information is transmitted to the host. Execution of this sequence allows immediate continuance of the analysis using an alternative reagent cassette, even if the above reagent cassette runs short of the reagent.

Furthermore, if the reagent cassette set in the main reagent buffer 4 is determined to require calibration and/or QC (quality control), these steps are conducted. Further, if the reagent cassette set in the subsidiary reagent buffer 12 is determined to require calibration and/or QC, the calibration follows the transfer of the particular reagent cassette to the main reagent buffer 4. A time required for these steps can be predicted. Discontinuation of the analysis due to a lack of the residual amount of reagent can therefore be prevented if the minimum allowable number of untested items is specified so that a sum of the time required for the transfer of the reagent cassette and the time required for the calibration and QC steps is shorter than a time required for the execution of the untested items for the reagent cassette usable for the same analysis as that conducted with the reagent cassette set in the main reagent buffer 4.

Furthermore, if a reagent cassette for which the calibration and/or QC step is not conducted is present in the subsidiary reagent buffer, this reagent cassette is transferred to the main reagent buffer in advance and the QC and/or calibration step is conducted.

Moreover, when reagent cassettes are to be set in the main reagent buffer 4, if reagents are already set in all reagent cassette-setting positions, a reagent cassette-setting position without a set reagent cassette needs to be created by unloading either reagent cassette before setting a desired reagent cassette. The setting of reagent cassettes may conducted after specification of analytical items for the biological sample, so required time for the setting of reagent cassettes should preferably be as short as possible.

In consideration of this, when the number of empty reagent cassette-setting positions decreases below a specified value, empty reagent cassette-setting positions can be ensured at all times by moving specific reagent cassettes from the main reagent buffer 4 to the subsidiary reagent buffer 12 until the number of empty reagent cassette-setting positions has equaled or exceeded the specified value. The specified value here is, for example, from 1 to nearly 4.

Details of control relating to creating empty positions on the reagent cassette plates in the automated analyzer according to the present embodiment are described below using FIG. 3.

Figure 3:
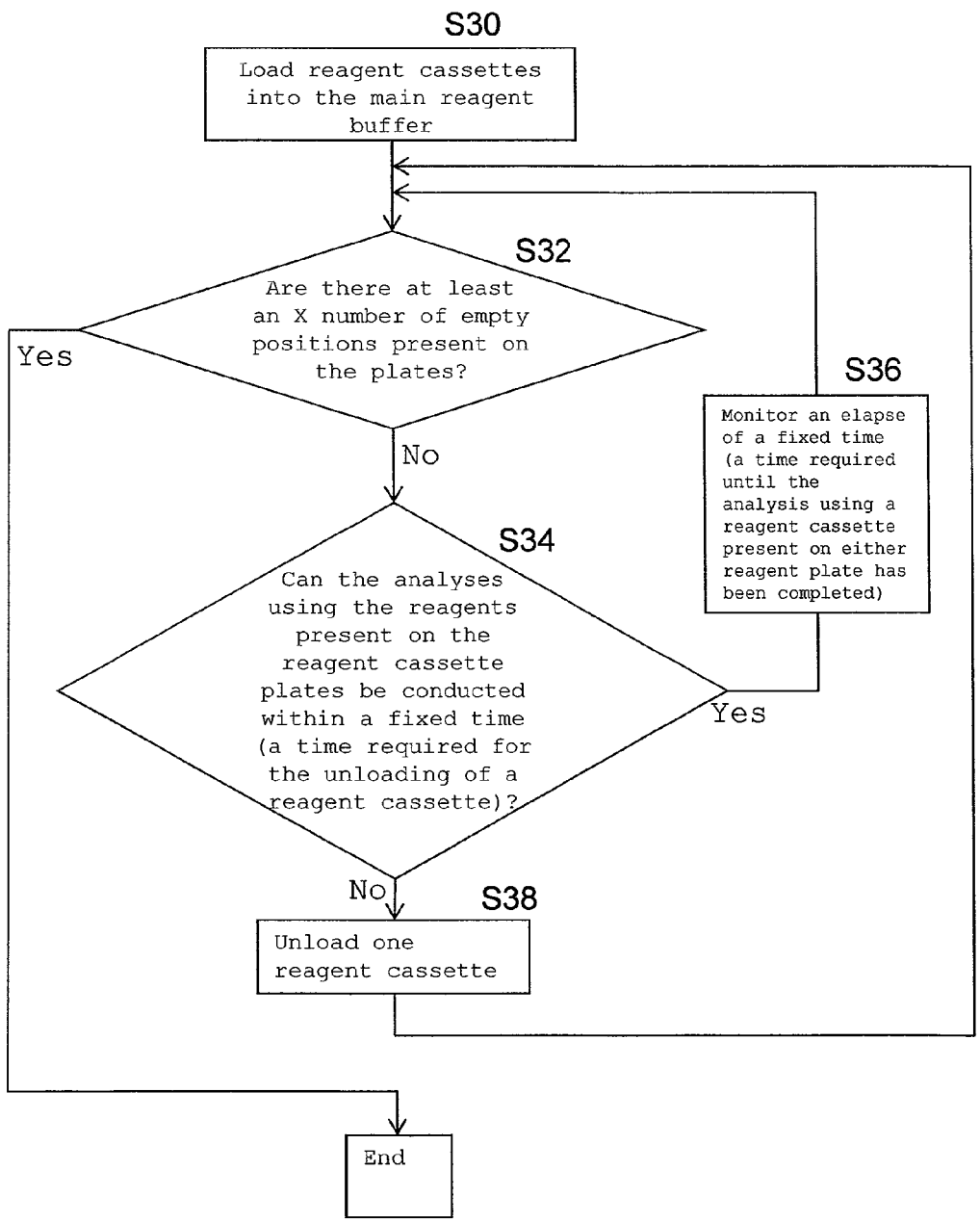
FIG. 3 is a flowchart that shows details of control relating to creating empty positions on reagent cassette plates in the automated analyzer according to the embodiment.

FIG. 3 is a flowchart showing the details of the control relating to creating empty positions on the reagent cassette plates in the automated analyzer according to the present embodiment.

In step S30, the control unit 200 loads reagent cassettes into the main reagent buffer 4.

Next, in step S32, the control unit 200 determines whether at least an X number of empty positions are present on the reagent cassette plates 13A, 13B. If at least the X number of empty positions are present, the control process is completed.

If in step S32 the number of empty positions is determined to be less than X, the control unit 200 determines in step S34 whether the analyses using the reagents present on the reagent cassette plates can be conducted within a fixed time (a time required for the unloading of a reagent cassette).

If the analyses can be conducted within the fixed time, in step S36 the control unit 200 monitors an elapse of a fixed time (a time required until the analysis using a reagent cassette present on either reagent cassette plate has been completed), and then upon the elapse of the fixed time, executes step S32 once again.

If in step S34 the analyses are determined not to be conducted within the fixed time, the control unit 200 unloads one reagent cassette in step S38.

The reagent cassette unloaded here will be, for example, one of two candidates, namely (1) a reagent cassette that cannot be used, even at a new request for the analysis, by reason of expiration of the reagent or an insufficiency in its residual amount, and (2) a reagent cassette infrequently used. First, the reagent cassette taken as example (1) above is transferred from the main reagent buffer 4 to the subsidiary reagent buffer 12. If the reagent cassette taken as example (1) is absent in the main reagent buffer 4, the reagent cassette taken as example (2) above is instead transferred from the main reagent buffer 4 to the subsidiary reagent buffer 12. Prior to the transfer, any reagent cassettes containing the reagent for which the analysis is not assigned within a fixed time existing after a need has arisen to unload the reagent cassette may be unloaded either in ascending order of frequency of use within a fixed time existing before the need arises to unload the reagent cassette, or in descending order of length of an elapsed time from immediately previous use of the reagent cassette. Such ordering of reagent cassette unloading enables highly efficient use of the reagent cassettes because reagent cassettes which are more frequently used than others can be collected in the main buffer 4. The standard that if the analysis is already completed, the reagent cassette is moved to the subsidiary reagent buffer, or if the analysis is not completed, the reagent cassette is moved to the main reagent buffer, can be applied to reagent cassettes for which calibration and/or QC has not been completed, as well as to reagent cassettes for calibration and/or QC has been completed. Although the operator specifies the fixed time in terms of the length of time or the number of tests, a time required for retransfer of the reagent cassette may instead be automatically calculated inside the device.

Additionally or alternatively, a specific reagent cassette, for example a cassette containing such a cleaning reagent, pretreatment reagent, or any other reagent that is very low in the frequency of use because the reagent is intended for maintenance only or for analytical items only, may usually be set in the subsidiary reagent buffer and only when a cleaning request or a pretreatment request is issued, may the reagent cassette be transferred to the main reagent buffer. After maintenance or the analysis using the reagent cassette, this cassette may be moved from the main reagent buffer to the subsidiary reagent buffer. Use of this sequence allows a larger number of reagent cassettes to be set in the main reagent buffer and used for analyses.

On the other hand, information on analytical items that have been executed in a certain period of time, for example one past week, may be stored and reagent cassettes that are larger in an execution count of analytical items may be preferentially stored into the main reagent buffer. Alternatively, reagent cassettes of higher priority levels may be stored into the main reagent buffer according to execution priority levels of analysis that have been defined for each analytical item specified by the operator. Use of this sequence allows a larger number of reagent cassettes of the higher priority levels of analysis to be set in the main reagent buffer. The priority levels of analysis are stored into a priority assignments table 210 of the control unit 200, shown in FIG. 1.

In addition, in a case that a time required for the setting of reagent cassettes is longer than a time required for the pipetting of reagents, if the reagent-pipetting operation being conducted on the first plate 13A of the main reagent buffer is completed earlier than the reagent cassette-setting operation being conducted on the second plate 13B, then even when next reagent needs to be pipetted into the reagent cassette set on the second plate 13B, the pipetting of the next reagent cannot be started until the currently underway setting of the reagent cassette on the second plate 13B has been completed. The analyses may be interrupted during that time.

An interruption in analyses, however, can be lessened by scheduling the analyses so that the analytical items involving the use of reagent cassettes set on the same plate will be continuously executed.

An analytical reordering method designed to shorten an interruption of analyses in the automated analyzer according to the present embodiment is described below using FIG. 4.

Figure 4:
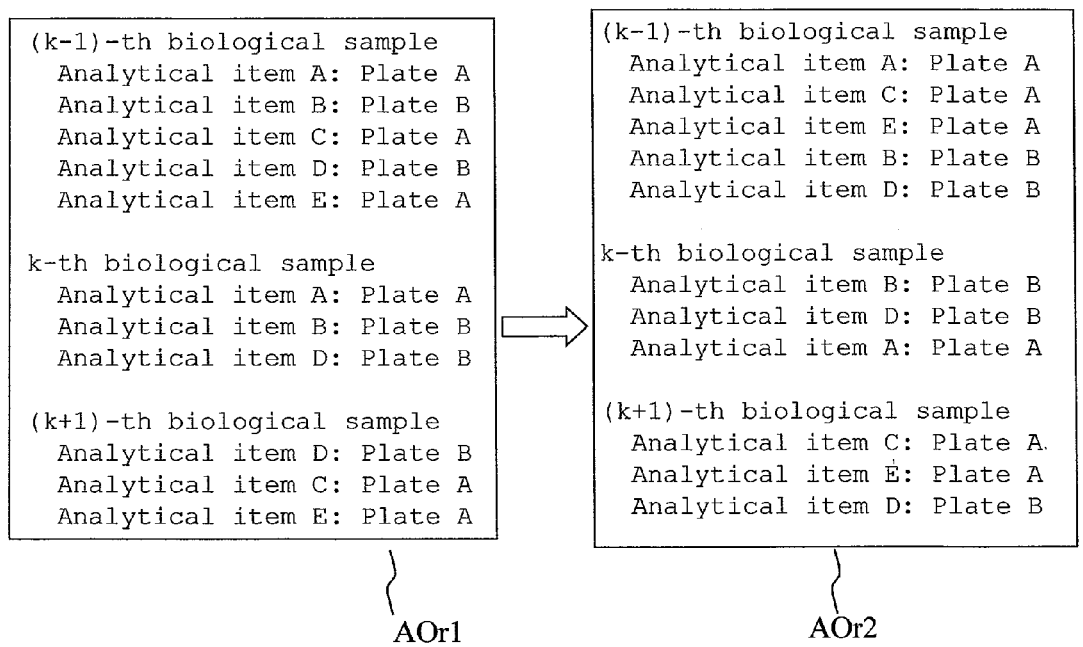
FIG. 4 is an explanatory diagram of an analytical reordering method designed to shorten an interruption of analyses in the automated analyzer according to the embodiment.

FIG. 4 is an explanatory diagram of the analytical reordering method designed to shorten the interruption of analyses in the automated analyzer according to the present embodiment.

For example, the analyses are scheduled so that as shown in FIG. 4, order AOr1 that has been input from the host or by the operator will be updated to order AOr2 in which the reagent-pipetting operation using the reagent cassettes set on the first plate 13A and the second plate 13B is repeated a plurality of times in succession. In this example, while the pipetting operation on plate A is being repeated the plurality of times, the setting of the reagent cassette on the second plate 13B is completed or a gap in time between the completion of the pipetting operation and that of the setting operation is reduced. Consequently, an interruption in the analyses can be prevented from occurring and/or an interruption time can be reduced.

In this way, an interruption in analyses can be lessened by scheduling the analyses so that the analytical items involving the use of reagent cassettes set on the same plate will be continuously executed.

Additionally or alternatively, as shown in FIG. 4, order of an analysis to be first conducted for a k-th biological sample (where "k" is an integer of 2 or more) among a plurality of biological samples to be continuously used, and order of an analysis to be lastly conducted for a (k−1)-th biological sample are scheduled so that the analyses will use reagent cassettes set on the same plate. Thus, a time for which the reagent cassettes set on the same plate are continuously used will be longer and an interruption in the analyses will be correspondingly lessened.

In this case, if the setting and unloading of the reagent cassettes require a time equivalent to an n-th number of reagent-pipetting repeat times (where "n" denotes a ratio of the time required for both kinds of operation and does not need to be an integer), the occurrence of an interruption in the analyses can be prevented by scheduling the analyses so that the items using the reagent cassettes set on the same plate will be continuously executed the number of times that is equal to an integer greater than "n".

Another analytical reordering method designed to shorten an interruption of analyses in the automated analyzer according to the present embodiment is described below using FIG. 5.

Figure 5:
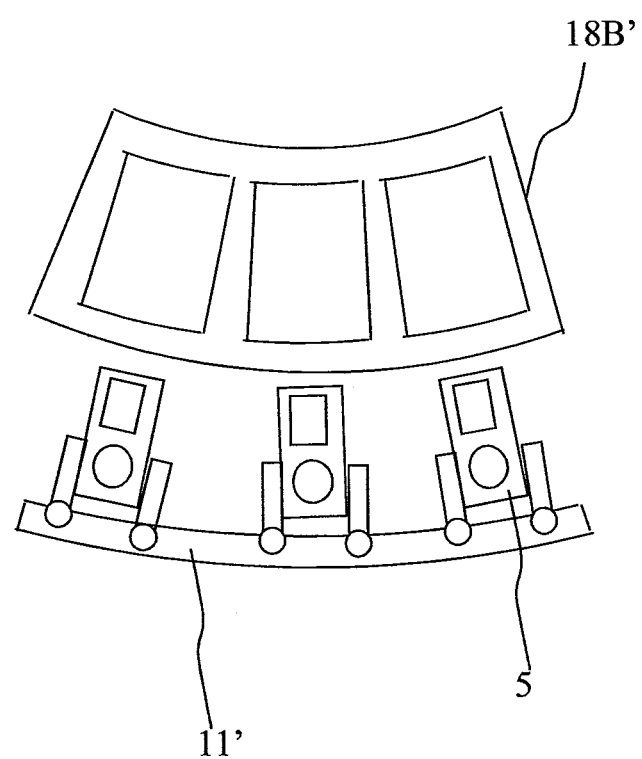
FIG. 5 is an explanatory diagram of another analytical reordering method designed to shorten the interruption of analyses in the automated analyzer according to the embodiment.

FIG. 5 is an explanatory diagram showing another example of an analytical reordering method designed to shorten the interruption of analyses in the automated analyzer according to the present embodiment.

One method of lessening the interruption of analyses is by, as shown in FIG. 5, setting or unloading a plurality of reagent cassettes 5 at the same time in or from the reagent cassette-setting positions at a reagent cassette loading/unloading port 18B' of the main reagent buffer 4 by means of a reagent cassette transfer 11'. Thus, frequency at which the plate is to be stopped for reagent cassette setting or unloading can be reduced and an analytical interruption time per unit time can also be reduced.

While the plate region in FIG. 1 is formed from two circular elements and rotationally moves with a central portion of the circles as a rotational center, the present invention can also be applied to a rectangular plate region that moves rectilinearly. In addition, the invention can be applied to a structure having a plurality of main reagent buffers and subsidiary reagent buffers, without being limited by the number of main reagent buffers and subsidiary reagent buffers.

As described above, in the present embodiment, a larger number of reagent cassettes can be used more efficiently by transferring buffer-stored reagent cassettes from the main reagent buffer to the subsidiary reagent buffer, and vice versa.

DESCRIPTION OF REFERENCE NUMBERS

1: Sample container hold position
2: Sampling position
3: Reaction vessel
4: Main reagent buffer
5: Reagent cassette
6A, 6B: Reagent pipetters
8: Reagent cassette scanner
9: Optical measuring unit
10: Reagent cassette insertion port
11, 11': Reagent cassette transfers
12: Subsidiary reagent buffer
13A, 13B: Plates
16: Reagent suction port
18A, 18B, 18B': Reagent cassette loading/unloading ports
20: Reaction disk
100: Analyzer body
200: Control unit
210: Priority assignments table
300: Display unit

The invention claimed is:

1. An automated analyzer comprising:
 a main reagent buffer including a plurality of plates disposed concentrically and configured to rotate independent of each other, each of the plurality of plates storing a plurality of reagent cassettes respectively containing a reagent used for analysis;
 a reagent pipetter for pipetting a desired reagent from the main reagent buffer into a reaction vessel containing a sample for analysis;
 a measurement device to analyze a mixture of the desired reagent and the sample contained in the reaction vessel;
 a subsidiary reagent buffer for storing a plurality of reagent cassettes each containing a reagent used for analysis;
 a reagent cassette transfer device configured to transfer the reagent cassettes from any of the plurality of plates of the main reagent buffer to the subsidiary reagent buffer, and configured to transfer reagent cassettes from the subsidiary reagent buffer to any of the plurality of plates of the main reagent buffer;

a control unit configured to control operation of the reagent cassette transfer device, the control unit includes a storage means, wherein the control unit is programmed to:

access from the storage means a predefined value for each of the plurality of plates, continuously determine if a number of reagent cassette-setting positions without a reagent cassette on a plate of the plurality of the plates of the main reagent buffer becomes less than the predefined value for the plate, and based on the determination, control the reagent cassette transfer device to unload the reagent cassettes from the main reagent buffer and transfer the unloaded reagent cassettes to the subsidiary reagent buffer until the number of reagent cassette-setting positions without a reagent cassette on each of the plates becomes equal to or greater than the predefined value for each of the plates, control the reagent pipetter to pipette a desired reagent from the main reagent buffer into the reaction vessel containing the sample for analysis, control the reagent cassette transfer device to transfer a reagent cassette from the subsidiary reagent buffer to any of the plurality of plates of the main reagent buffer and load the reagent cassette into the main reagent buffer, control the reagent cassette transfer device to unload the reagent cassettes from the main reagent buffer and transfer the unloaded reagent cassettes to the subsidiary reagent buffer during pipetting of the desired reagent from the main reagent buffer into the reaction vessel containing the sample for analysis, wherein the reagent cassette transfer device transfers the reagent cassettes from the main reagent buffer to the subsidiary reagent buffer, and vice versa along one fixed path that extends between the main reagent buffer and the subsidiary reagent buffer along a radial direction with respect to the plurality of plates of the main reagent buffer.

2. The automated analyzer according to claim 1, wherein the control unit is further programmed to control the reagent cassette transfer device to transfer, from the main reagent buffer to the subsidiary reagent buffer, the reagent cassettes which will not be used for analysis during a period of time defined as an amount of time required for a reagent cassette to be reloaded after being unloaded, and to transfer one or more reagent cassettes to the main reagent buffer when the number of reagent cassette-setting positions without a reagent cassette on a plate of the main reagent buffer becomes greater than the predefined values for each of the plates.

3. The automated analyzer according to claim 1, wherein the control unit is further programmed to control the reagent cassette transfer device to preferentially transfer reagent cassettes having respective times of being unused for analysis longer than a predefined time from the main reagent buffer to the subsidiary reagent buffer when the number of reagent cassette-setting positions without a reagent cassette on the plate of the main reagent buffer becomes less than the predefined value for the plate.

4. The automated analyzer according to claim 1, wherein the control unit is further programmed to schedule an order of analysis using reagent cassettes placed on a same plate for a plurality of samples so that reagent cassettes on the same plate will be continuously used, the samples being continuously analyzed according to a plurality of analytical request items assigned thereto.

5. The automated analyzer according to claim 1, wherein the stored predefined value for each of the plurality of plates is at least two.

6. The automated analyzer according to claim 1, wherein the reagent cassette transfer device is disposed outside an outer circumference of the main reagent buffer.

* * * * *